US010857007B2

(12) United States Patent
Wilson (10) Patent No.: US 10,857,007 B2
(45) Date of Patent: Dec. 8, 2020

(54) COUPLING FOR A PROSTHETIC DEVICE

(71) Applicant: Michael Thomas Wilson, Missouri City, TX (US)

(72) Inventor: Michael Thomas Wilson, Missouri City, TX (US)

( * ) Notice: Subject to any disclaimer, the term of this patent is extended or adjusted under 35 U.S.C. 154(b) by 190 days.

(21) Appl. No.: 15/751,837

(22) PCT Filed: Aug. 10, 2016

(86) PCT No.: PCT/US2016/046258
§ 371 (c)(1),
(2) Date: Feb. 9, 2018

(87) PCT Pub. No.: WO2017/027543
PCT Pub. Date: Feb. 16, 2017

(65) Prior Publication Data
US 2018/0235780 A1   Aug. 23, 2018

Related U.S. Application Data

(60) Provisional application No. 62/204,221, filed on Aug. 12, 2015.

(51) Int. Cl.
*A61F 2/66* (2006.01)
*B29C 65/70* (2006.01)
(Continued)

(52) U.S. Cl.
CPC .............. *A61F 2/6607* (2013.01); *A61F 2/66* (2013.01); *B29C 65/70* (2013.01); *A61F 2002/5001* (2013.01); *A61F 2002/507* (2013.01); *A61F 2002/5009* (2013.01); *A61F 2002/5067* (2013.01); *A61F 2002/5086* (2013.01); *A61F 2002/5096* (2013.01);
(Continued)

(58) Field of Classification Search
CPC ........ A61F 2002/507; A61F 2002/5067; A61F 2002/5086; A61F 2002/5096; A61F 2/6607; A61F 2/76
See application file for complete search history.

(56) References Cited

U.S. PATENT DOCUMENTS 3,956,775 A   5/1976   Moore
4,134,159 A   1/1979   Wilson
(Continued)

OTHER PUBLICATIONS

International Patent Application No. PCT/US2016/046258 International Search Report and Written Opinion dated Oct. 26, 2016 (14 pages).

*Primary Examiner* — Christie L Bahena
(74) *Attorney, Agent, or Firm* — Conley Rose, P.C.

(57) ABSTRACT

A prosthetic foot, including a keel having a longitudinal axis. The keel includes a keel body including a heel portion, a forefoot portion, and an ankle portion positioned between the heel portion and the forefoot portion. The ankle portion includes a housing having a vertically oriented central axis. In addition, the prosthetic foot includes a coupling assembly disposed within the housing of the ankle portion. The coupling assembly includes a bearing member disposed about the central axis, a support sleeve concentrically disposed about the bearing member, and an embedding member disposed about the support sleeve. The embedding member includes a plurality of interlocking rings.

19 Claims, 5 Drawing Sheets

(51) Int. Cl.
  *A61F 2/50*    (2006.01)
  *B29L 31/00*   (2006.01)
(52) U.S. Cl.
  CPC . *A61F 2002/665* (2013.01); *A61F 2002/6642* (2013.01); *A61F 2002/6657* (2013.01); *B29L 2031/7532* (2013.01)

(56) References Cited

U.S. PATENT DOCUMENTS

| | | | | |
|---|---|---|---|---|
| 4,221,007 | A | * | 9/1980 | Wilson ............... A61F 2/76 623/38 |
| 4,283,800 | A | | 8/1981 | Wilson |
| 4,645,508 | A | * | 2/1987 | Shorter ............ A61F 2/6607 623/48 |
| 5,112,356 | A | * | 5/1992 | Harris ............... A61F 2/66 623/49 |
| 6,511,514 | B1 | | 1/2003 | Wilson |
| 2006/0271200 | A1 | * | 11/2006 | Greenlee ............ A61F 2/32 623/22.16 |
| 2007/0203585 | A1 | | 8/2007 | Wilson |
| 2009/0234463 | A1 | * | 9/2009 | Wilson ............... A61F 2/66 623/55 |
| 2014/0243997 | A1 | | 8/2014 | Clausen et al. |

* cited by examiner

COUPLING FOR A PROSTHETIC DEVICE

CROSS-REFERENCE TO RELATED APPLICATIONS

This application is a National Phase entry, and claims priority to, PCT Application No. PCT/US2016/046258, filed Aug. 10, 2016, which claims the benefit of U.S. provisional patent application Ser. No. 62/204,221 filed Aug. 12, 2015, and entitled "Coupling For A Prosthetic Device," the entire contents of each being hereby incorporated herein by reference for all purposes.

STATEMENT REGARDING FEDERALLY SPONSORED RESEARCH OR DEVELOPMENT

Not applicable.

BACKGROUND

This disclosure relates generally to prosthetic limbs. More particularly, this disclosure relates to couplings for coupling a prosthetic foot to an amputee's limb or extremity.

A useful prosthesis should at least partially simulate the operation and motion of an anatomical foot. In addition, for Syme amputees (e.g., amputees who have sustained an ankle disarticulation), a useful prosthesis should simulate the operation, flexion, and motion of an anatomical ankle. The terms "anatomical foot" and "anatomical ankle" are used herein to refer to the foot and ankle, respectively, of a human body.

An anatomical foot, including the ankle joint, is capable of motion around three perpendicular axes, as well as varying degrees of flexure. Specifically, the anatomical foot and ankle are capable of dorsiflexion, planiflexion, inversion, eversion, and transverse rotation. Dorsiflexion and planiflexion comprise the movement of the ball of the foot upward and downward, respectively, with respect to the heel. Inversion and eversion are the twisting of the foot around its longitudinal axis, resulting in outward and inward tilting of the ankles, respectively. Transverse rotation occurs when the foot rotates with respect to the longitudinal axis of the leg, such as occurs during left and right turns of the body.

A prosthetic foot may include a distinct prosthetic ankle capable of complicated motion (e.g., motion around two or three axes). In particular, such prosthetics may be useful for Syme amputees since the inclusion of a prosthetic ankle may simulate the operation, flexion, and motion normally provided by an anatomical ankle.

BRIEF SUMMARY OF THE DISCLOSURE

Some embodiments disclosed herein are directed to prosthetic feet. In an embodiment, a prosthetic foot includes a keel having a longitudinal axis. The keel includes a keel body including a heel portion, a forefoot portion, and an ankle portion positioned between the heel portion and the forefoot portion. The ankle portion includes a housing having a vertically oriented central axis. In addition, the prosthetic foot includes a coupling assembly disposed within the housing of the ankle portion. The coupling assembly includes a bearing member disposed about the central axis, a support sleeve concentrically disposed about the bearing member, and a embedding member disposed about the support sleeve. The embedding member includes a plurality of interlocking rings.

Other embodiments disclosed herein are directed to coupling assemblies for use within prosthetic feet. In an embodiment, a coupling assembly has a central axis and includes a bolt including an externally threaded shaft that extends along the central axis. In addition, the coupling assembly includes a bearing member disposed concentrically disposed about the bolt. Further, the coupling assembly includes a support sleeve concentrically disposed about the bearing member. Still further, the coupling assembly includes an embedding member disposed about the support sleeve. The embedding member includes a plurality of interlocking rings secured to a radially outer surface of the support sleeve.

Still other embodiments disclosed herein are directed to a method of making a prosthetic foot. In an embodiment, the method includes installing a coupling assembly within a mold. The coupling assembly includes a bearing member disposed along a central axis, a support sleeve concentrically disposed about the bearing member, and an embedding member disposed about the support sleeve. The embedding member includes a plurality of interlocking rings secured to an outer surface of the support sleeve. In addition, the method includes filling the mold with a material such that the material flows around and through the interlocking rings of the embedding member. Further, the method includes forming a keel of the prosthetic foot out of the material.

Embodiments described herein comprise a combination of features and characteristics intended to address various shortcomings associated with certain prior devices, systems, and methods. The foregoing has outlined rather broadly the features and technical characteristics of the disclosed embodiments in order that the detailed description that follows may be better understood. The various characteristics and features described above, as well as others, will be readily apparent to those skilled in the art upon reading the following detailed description, and by referring to the accompanying drawings. It should be appreciated that the conception and the specific embodiments disclosed may be readily utilized as a basis for modifying or designing other structures for carrying out the same purposes as the disclosed embodiments. It should also be realized that such equivalent constructions do not depart from the spirit and scope of the principles disclosed herein.

BRIEF DESCRIPTION OF THE DRAWINGS

For a detailed description of various exemplary embodiments, reference will now be made to the accompanying drawings in which.

DETAILED DESCRIPTION OF EXEMPLARY EMBODIMENTS

The following discussion is directed to various exemplary embodiments. However, one of ordinary skill in the art will understand that the examples disclosed herein have broad application, and that the discussion of any embodiment is meant only to be exemplary of that embodiment, and not intended to suggest that the scope of the disclosure, including the claims, is limited to that embodiment.

The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection of the two devices, or through an indirect connection that is established via other devices, components, nodes, and connections. In addition, as used herein, the terms "axial" and "axially" generally mean along or parallel to a given axis (e.g., central axis of a body or a port), while the terms "radial" and "radially" generally mean perpendicular to the given axis. For instance, an axial distance refers to a distance measured along or parallel to the axis, and a radial distance means a distance measured perpendicular to the axis.

As previously described, some amputees (e.g., Syme amputees) may benefit from a prosthetic foot that includes a prosthetic ankle capable of complicated motion (e.g., motion around two or three axes) to simulate the operation, flexion, and motion normally provided by an anatomical ankle. However, inclusion of such a prosthetic ankle may add bulk and additional weight to the prosthesis. The additional weight may result in a prosthesis that is too heavy for some patients, such as geriatric patients, very young patients, patients who suffer some degree of muscular weakness, or patients who simply prefer a lighter prosthesis. In addition, although some flexibility may be desirable, a prosthetic foot should provide a secure and relatively rigid means for coupling the prosthetic foot to the amputee. Such a coupling means should be sufficiently strong to support its wearer, and sufficiently durable to withstand the stresses of repeated use over long periods of time. However, depending on the construction of the prosthetic, particularly the coupling between any molded materials and underlying structural components, stress concentrations proximal the areas where the prosthetic foot flexes may develop and leads to premature weakening, cracking, or breaking of the prosthetic foot. Thus, disclosed herein are embodiments of improved prosthetic feet that include a coupling assembly for connecting the foot to a pylon or other component that supports complicated motion at the ankle and reduces the concentration of stresses to minimize premature wear of the foot.

Figure 1:
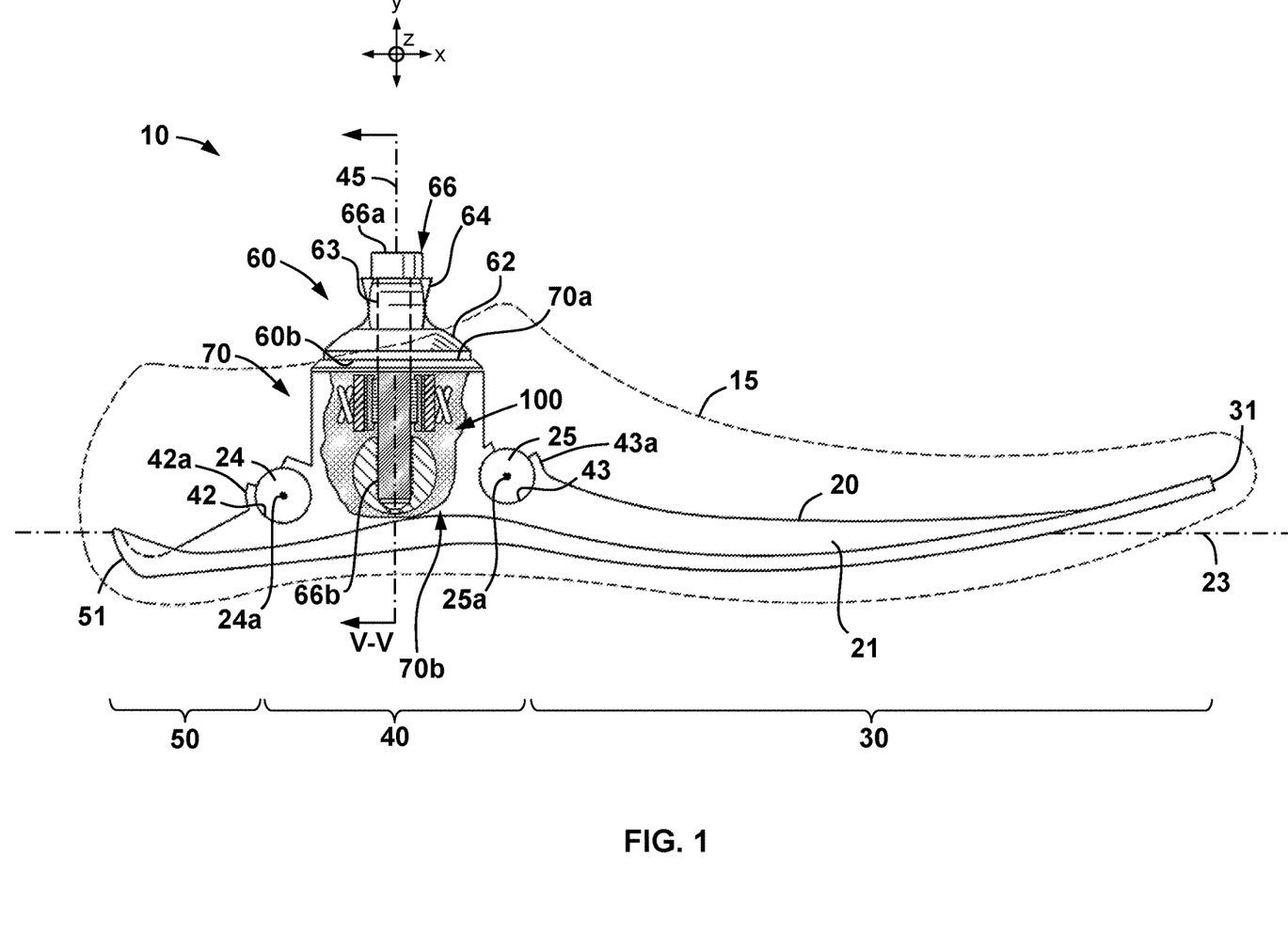
FIG. 1 is a side, partial cross-sectional view of an embodiment of a prosthetic foot in accordance with principles disclosed herein.

For purposes of clarity and further explanation, the x, y, and z-axes are shown in FIG. 1 and have been assigned as follows: the x-axis is perpendicular to the longitudinal axis of the leg and parallel to the longitudinal axis of the foot; the y-axis is parallel to the longitudinal axis of the leg; and the z-axis is perpendicular to the longitudinal axis of the leg and the longitudinal axis of the foot, generally passing through the lateral sides of the ankle. Generally, inversion and eversion (e.g., the twisting of the foot about its longitudinal axis) may occur about the x-axis, transverse rotation (rotation of the foot with respect to the longitudinal axis of the leg) may occur about the y-axis, and dorsiflexion and planiflexion (e.g., movement of the ball of the foot upward and downward, respectively) may occur about the z-axis. It is to be understood that the three axes (x-axis, y-axis, and z-axis) are orthogonal.

Figure 2:
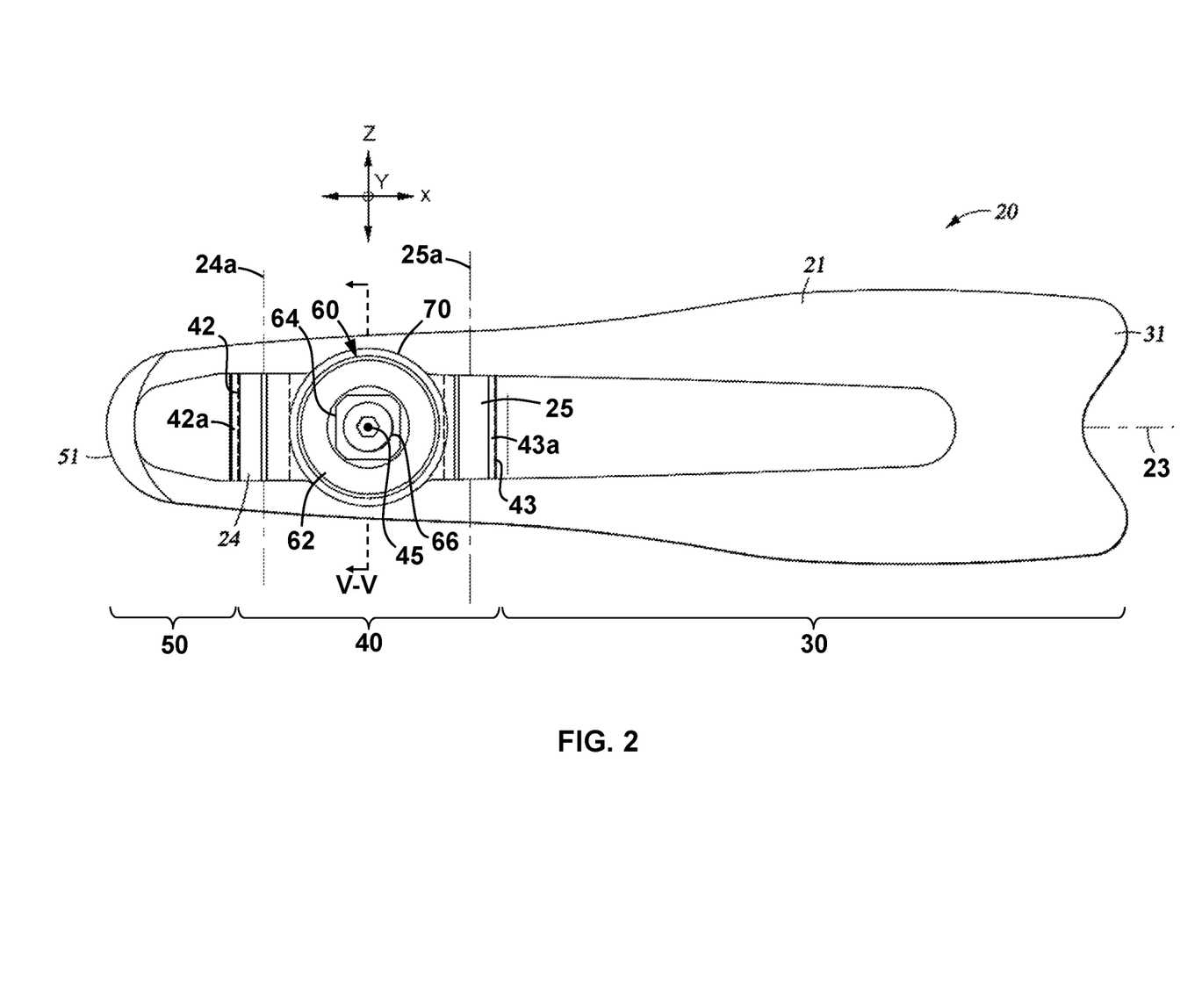
FIG. 2 is a top view of the prosthetic foot of FIG. 1.

Referring now to FIGS. 1 and 2, an embodiment of a prosthetic foot 10 is shown. Foot 10 includes a keel 20 and a cosmesis 15 (shown in phantom in FIG. 1). Cosmesis 15 substantially surrounds keel 20 and provides the external appearance of prosthetic foot 10. In this embodiment, cosmesis 15 is made of foamed polyethylene and ethylene-vinyl acetate copolymer (EVA). In select embodiments, the inside of the cosmesis is formed of expanded polyethylene and the outside is formed of expanded EVA, which offers the potential for improved abrasion resistance. Keel 20 comprises a keel body 21, a first or rear ankle bumper 24 coupled to keel body 21, and a second or front ankle bumper 25 coupled to keel body 21. Keel 20 extends along a longitudinal axis 23 from a heel end 51 to a toe end 31. Together, keel 20 and cosmesis 15 closely replicate the structure and form of an anatomical foot, including the ankle joint.

Referring still to FIGS. 1 and 2, in general, keel body 21 may be made of any suitable material(s) including, without limitation, polymers (e.g., plastic), composites (e.g., carbon fiber and epoxy composite), or combinations thereof. However, keel body 21 is preferably made of a rigid or semi-rigid material with sufficient strength to bear the weight and loads applied by the patient (or user or wearer, etc.). In addition, to minimize the bulk and weight of keel 20 and prosthetic foot 10, keel body 21 is preferably made of a relatively lightweight material, and further, to more closely simulate the flexibility and flexion of an anatomical foot, keel body 21 is preferably made of a resilient material capable of flexing under loads, and capable of returning to its unflexed state upon removal of any applied loads. Exemplary materials suitable for the keel body 21 include polypropylene or a polypropylene-polyethylene blend preferably employing a low molecular weight polyethylene. Without being limited by this or any particular theory, in those embodiments where the keel body 21 comprises a polypropylene-polyethylene blend, the greater the percentage of polyethylene (by weight), the greater the flexibility and softness of the keel body, whereas the greater the polypropylene, the greater the stiffness and resiliency of the keel body 21. In general, the keel body 21 can be formed by any suitable method including, without limitation, molding, casting, machining, or combinations thereof. In embodiments where keel body 21 comprises a polymer such as polypropylene or a polypropylene-polyethylene blend, keel body 21 is preferably formed by injection molding or compression molding. In this embodiment, keel body 21 is a unitary, monolithic single piece made of polypropylene via compression molding.

Keel body 21 is generally divided into a forefoot portion 30, a heel portion 50, and a mid-foot or ankle portion 40 extending between forefoot portion 30 and heel portion 50. Forefoot portion 30 and heel portion 50 may be substantially the same as similar components described in U.S. Pat. No. 8,118,879, the contents of which are incorporated herein by reference in their entirety for all purposes. In addition, it should be appreciated that heel portion 50 and forefoot portion 30 may include other designs and arrangements while still being within scope of this disclosure.

Referring still to FIGS. 1 and 2, ankle portion 40 of keel body 21 includes a cylindrical housing 70 that surrounds and encloses a coupling assembly 100 that supports a connector 60. In other words, assembly 100 couples connector 60 to ankle portion 40 of keel body 21. In addition, ankle portion 40 includes a first bumper capture cavity 42 that receives a first bumper 24 and a second bumper capture cavity 43 that receives a second bumper 25. Housing 70 is axially positioned between first pump capture cavity 42 and second bumper capture cavity 43 with respect to axis 23. Thus, cavities 42, 43 and corresponding bumpers 24, 25, respectively, are disposed on opposite sides of housing 70.

As best shown in FIG. 1, cylindrical housing 70 has a vertically oriented central axis 45, an upper end 70a distal the remainder of keel body 21, and a lower end 70b that is contiguous and formed as a single piece with the remainder of keel body 21. Axis 45 is substantially parallel with the y-axis and substantially perpendicular to longitudinal axis 23 of keel 20. As best shown in the top view of FIG. 2, in this embodiment, central axis 45, and hence housing 70, is centered relative to ankle portion 40. In other embodiments, housing 70 may be positioned off center relative to the ankle portion (e.g., ankle portion 40).

Referring still to FIGS. 1 and 2, connector 60 includes a semi-spherical dome 62, a connecting spindle 64 extending upward from dome 62, and a throughbore 63 extending through spindle 64 and dome 62. In this embodiment, dome 62, spindle 64, and throughbore 63 are coaxially aligned with vertical axis 45. Connecting spindle 64 couples keel 20, and hence prosthetic foot 10, to an amputee. For example, in this embodiment, connecting spindle 64 is received and secured by a mating socket mounted on the lower end of a liner worn by the amputee (or a pylon coupled to the liner). Consequently, spindle 64 is preferably provided at its upper end with a standard square prosthetic connector, such as an OTTOBOCK™ connector or the like.

To provide a stable and predictable connection between the amputee and keel 20, connector 60 (including spindle 64) is rigidly secured to keel body 21 such that there is little to no relative movement between connector 60 and keel body 21. In this embodiment, a bolt 63 and coupling assembly 100 rigidly couple connector 60 to keel body 21 such that connector 60 is rotationally and translationally fixed relative to keel body 21. Bolt 66 extends through bore 63 and threadably engages coupling assembly 100 (described in more detail below), which is embedded in ankle portion 40 of keel body 21. To further limit rotational movement of connector 60 relative to keel body 21 in this embodiment, a lower surface 60b of connector 60 is textured to enhance frictional engagement with upper end 70a of housing 70 as bolt 66 compresses connector 60 against housing 70. For example, lower surface 60b may be textured in the manner described in U.S. Pat. No. 8,118,879, the entire contents being previously incorporated by reference above.

Once spindle 64 is coupled to the amputee, dome 62 bears the majority of the loads (e.g., weight) applied to keel body 21 by an amputee wearing prosthetic foot 10. Dome 62 preferably has relatively smooth surface to enhance the engagement with other components (e.g., the pylon, socket, etc.). Moreover, it should be appreciated that dome 62 has a semi-spherical geometry in this embodiment. The semi-spherical geometry allows for a variety of orientations of prosthetic foot 10 relative to an amputee when prosthetic foot 10 is coupled to the amputee. In particular, the semi-spherical geometry of dome 62 may permit the adjustment of foot 10 about the x-axis, the y-axis, and the z-axis, relative to the amputee. For example, when foot 10 is fitted to an amputee by an OTTOBOCK™ connector, the orientation of foot 10 may be adjusted about three axes by varying the position of the female socket of the OTTOBOCK™ connector relative to dome 62. Moreover, this feature of dome 62 allows subsequent adjustments of foot 10 about any of the three axes without the need to re-design foot 10. In the embodiment shown in FIGS. 1 and 2, dome 62 is integral with spindle 64 (as connector 60) and distinct from keel body 21 (i.e., dome 62 and spindle 64 are monolithic and made from a single piece of material). However, in other embodiments, the dome (e.g., dome 62) may be defined by, and integral with, the keel body (e.g., keel body 21) and distinct from spindle 64 (e.g., in some embodiments dome 62 may be threadably engaged with connector spindle 64). To enhance durability and strength, dome 62 and spindle 64 are preferably made from a durable, rigid material such as a metal or a metal alloy (e.g., such as Grade 5 titanium or 7068 aluminum alloy). In this embodiment, dome 62 and spindle 64 are made from Grade 5 titanium.

Referring still to FIGS. 1 and 2, keel 20 includes bumpers 24, 25 disposed in capture cavities 42, 43, respectively, as previously described. In general, bumpers 24, 25 are employed to simulate the anatomical ankle. To more closely simulate the location, flexion, and feel of the anatomical ankle, the position of each bumper 24, 25 along the longitudinal axis 23 is preferably as close as possible to axis 45, which generally represents that center of the anatomical ankle. As best shown in the top view of FIG. 2, in the embodiments described herein, bumpers 24, 25 are disposed along longitudinal axis 23 immediately adjacent dome 62 and housing 70, with bumper 24 just rearward of dome 62 (and housing 70) and bumper 25 just forward of dome 62 (and housing 70). Although two bumpers 24, 25 are shown in FIGS. 1 and 2, in other embodiments, fewer or more bumpers may be provided.

Bumpers 24, 25 are secured within capture cavities 42, 43, respectively, such that bumpers 24, 25 are fixed translationally or rotationally relative to keel body 21. To sufficiently retain each bumper 24, 25, more than half of the outer perimeter of each bumper 24, 25 (i.e., more than half the outer perimeter at each cross-section of bumpers 24, 25 perpendicular to the longitudinal length thereof) is preferably engaged by keel body 21. In this embodiment, each capture cavity 42, 43 extends around about 70% to 80% of the outer perimeter of each bumper 24, 25, respectively. In particular, a pair of opposed retention lips 42a, 43a extend from each capture cavity 42, 43, respectively, around a portion of the outer circumference of each bumper 24, 25, respectively, to sufficiently secure each bumper 24, 25, respectively, therein. Bumpers 24, 25 may be molded into keel body 21 or inserted after keel body 21 has been formed.

In this embodiment, each bumper 24, 25 is cylindrical, and includes a central axis 24a, 25a, respectively, oriented substantially perpendicular to longitudinal axis 23 and central axis 45. Consequently, bumpers 24, 25 may also be described as "transverse." In this embodiment, the diameter of each bumper 24, 25 (i.e., the outer diameter of each cross-section of bumpers 24, 25 perpendicular to axes 24a, 25a, respectively) is substantially the same, however, in other embodiments, the diameter of each bumper (e.g., bumpers 24, 25) may be different. In other embodiments, one or more of the bumpers (e.g., bumpers 24, 25) may have a non-circular cross-section such as rectangular, triangular, or oval. The inner surfaces of the capture cavities 42, 43 preferably engage and mate with the outer surfaces of the bumpers 24, 25 such that forces may be directly transferred therebetween. Consequently, in this embodiment, the inner surfaces of capture cavities 42, 43 are cylindrical and engage the outer surfaces of bumpers 24, 25, respectively. Moreover, in addition to the features discussed above bumpers 24, 25 may be configured (e.g., sized, shaped, positioned) substantially the same as the bumpers disclosed in U.S. Pat. No. 8,118,897, the entire contents being previously incorporated by reference above.

To more closely simulate an anatomical ankle, each bumper 24, 25 comprises a compressible and resilient material that is softer (i.e., has a lower durometer hardness) than keel body 21. In particular, bumpers 24, 25 are preferably made of materials having durometer hardnesses between 60 and 100. In this embodiment, rear bumper 24 is preferably made from a material having a durometer hardness between 65 and 75, and more preferably a durometer hardness of about 70, whereas front bumper 25 is preferably made from a material having a durometer hardness between 75 and 100, and more preferably a durometer hardness between 80 and 90. In other embodiments, bumpers 24, 25 may have the same or similar hardnesses. The materials, and associated durometer hardnesses, of bumpers 24, 25 may vary depending on a variety of factors including, without limitation, the length of the keel 20 along axis 23, the expected activities of the amputee, the amputee's age, the desired flexibility, or combinations thereof. Suitable materials for bumpers 24, 25 include, without limitation, Buna-N rubber and urethane. For a keel body 21 made of polypropylene or polypropylene-polyethylene blend, and bumpers 24, 25 made of a material with a durometer hardness between 60 and 100 (e.g., Buna-N rubber), the diameter of each bumper 24, 25 is preferably about ¼ inch to ¾ inch, and more preferably about ⅜ inch to ⅝ inch. The diameter of each bumper 24, 25 is preferably increased as the overall length of keel 20 increases along axis 23.

Figure 3:
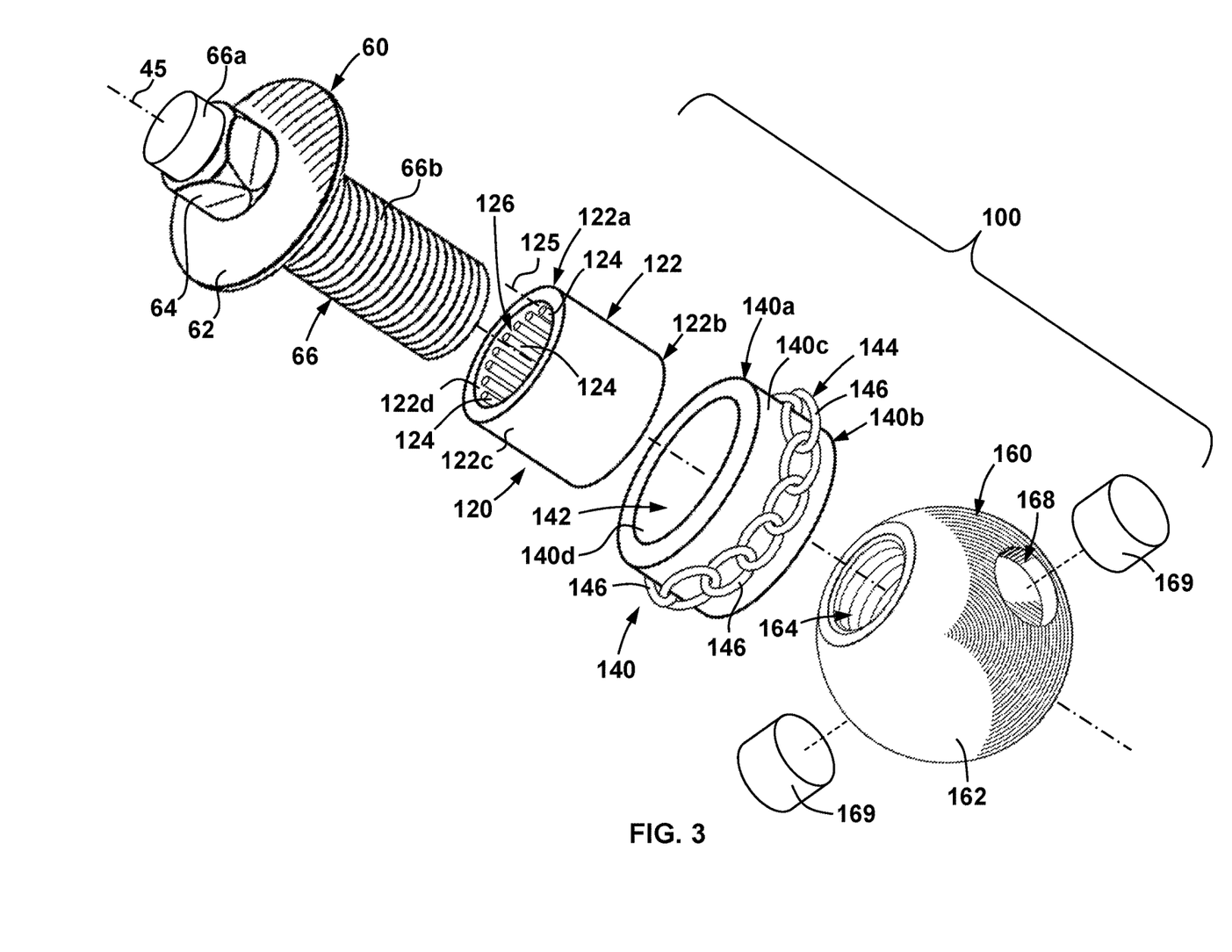
FIG. 3 is an exploded perspective view of the coupling assembly of FIG. 1.
Figure 4:
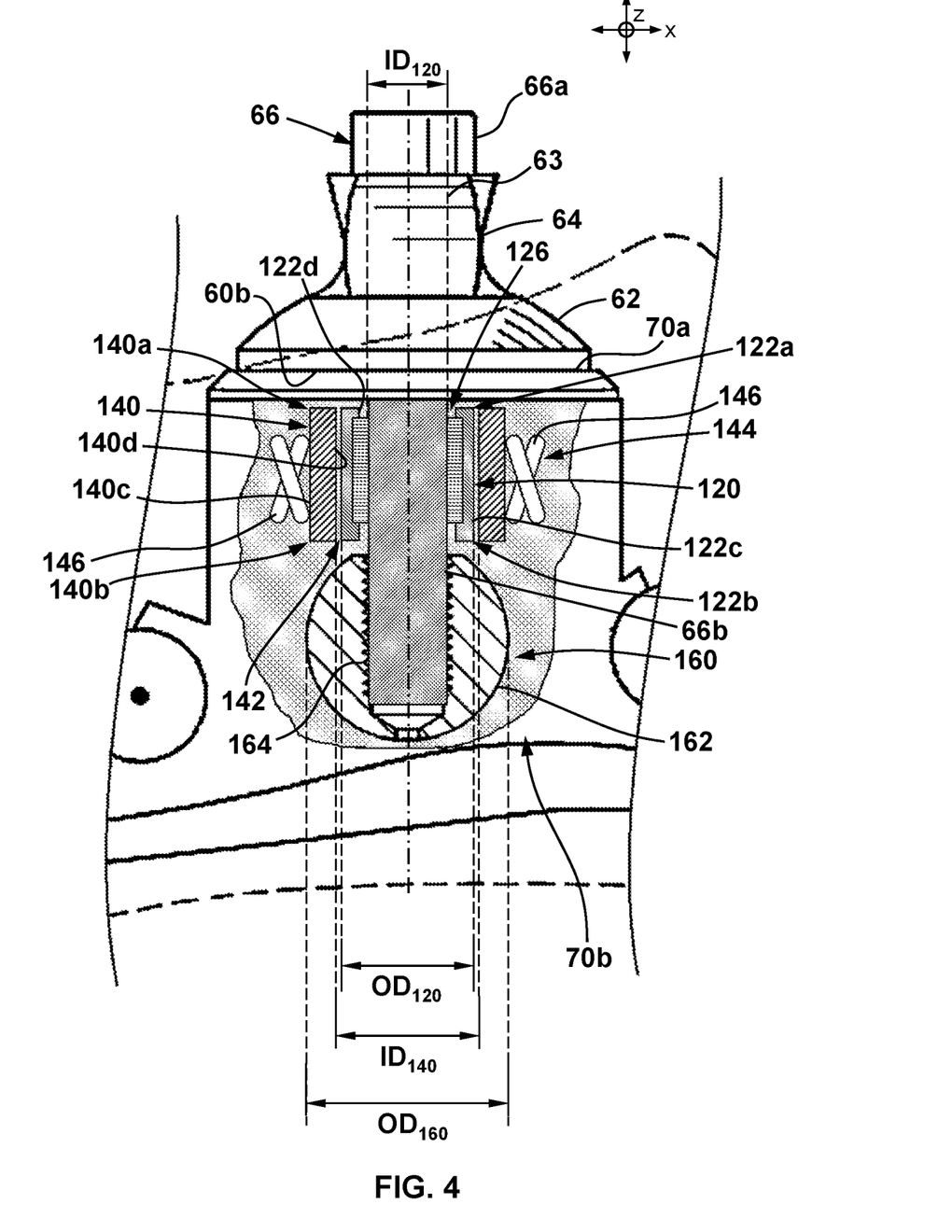
FIG. 4 is an enlarged, partial side cross-sectional view of the prosthetic foot of FIG. 1.

Referring now to FIGS. 1, 3, and 4, coupling assembly 100 is embedded within housing 70 of ankle portion 40 and is disposed about and coaxially aligned with axis 45. In this embodiment, coupling assembly 100 includes an annular bearing member 120, an annular support sleeve 140 concentrically disposed about bearing member 120, and a ball 160 disposed axially below bearing member 120 and sleeve 140 with respect to axis 45.

In general, bearing member 120 can comprise any suitable member for accommodating limited bending of a centrally received member (e.g., bolt 66) relative to a central axis (e.g., axis 45, y-axis). In this embodiment, bearing member 120 is a needle bearing including an annular race 122 and a plurality of elongate bearing elements 124 rotatably coupled to race 122. Race 122 is an annular sleeve that includes a first or upper end 122a, a second or lower end 122b opposite upper end 122a, a radially outer cylindrical surface 122c extending axially between ends 122a, 122b, and a radially inner cylindrical surface 122d extending axially between ends 122a, 122b. Inner surface 122d defines a throughbore 126 extending between ends 122a, 122b. As is best shown in FIG. 3, bearing members 124 are uniformly circumferentially-spaced about inner surface 122d, and are rotatably disposed in mating recesses disposed along inner surface 122d. Consequently, each bearing member 124 is free to rotate relative to race 122 about a corresponding axis of rotation 125 oriented parallel to axis 45. Members 124 define a minimum inner diameter $ID_{120}$ of bearing member 120 (see FIG. 4). Outer surface 122c is a smooth cylindrical surface defining the outer diameter $OD_{120}$ of bearing member 120.

Referring still to FIGS. 1, 3, and 4, support sleeve 140 is an annular member that includes a first or upper end 140a, a second or lower end 140b opposite upper end 140a, a radially outer cylindrical surface 140c extending axially between ends 140a, 140b, and a radially inner cylindrical surface 140d also extending axially between ends 140a, 140b. Inner surface 140d defines a throughbore 142 extending between ends 140a, 140b. As best shown in FIG. 4, throughbore 142 has an inner diameter $ID_{140}$ that is substantially equal to or slightly larger than the outer diameter $OD_{120}$ of bearing member 120 such that bearing member 120 can be received into throughbore 142 and slidingly engage sleeve 140 as shown. In some embodiments, sleeve 140 is made of chrome-moly (which comprises molybdenum and chromium); however, sleeve 140 may be made of other materials (e.g., metals) in other embodiments.

An embedding member 144 is disposed about sleeve 140 and attached to radially outer surface 140c. In this embodiment, embedding member 144 includes a plurality of individual rings 146 that form a chain extending circumferentially around support sleeve 140 with respect to axis 45. One or more of the rings 146 are rigidly and fixably secured to outer surface 140c such that embedding member 144 does not move translationally or rotationally relative to sleeve 140. In general, rings 146 can be secured to outer surface 140c in any suitable manner, such as, for example, adhesives, bonding, welding, soldering, etc. In this embodiment, one or more of the rings 146 are welded to radially outer surface 140c of sleeve 140. As will be explained in more detail below, during molding of keel body 21, molded material is flowed or otherwise extruded around and between rings 146 such that member 144 and support sleeve 140 attached to member 144 are firmly embedded within body 21 (particularly housing 70 of ankle portion 40). In some embodiments, rings 146 are harder and less flexible than the molded materials making up keel body 21, but are more flexible than the materials making up sleeve 140 and bearing member 120. In other words, rings 146 are more stiff (i.e., have a higher stiffness) than the molded materials making up keel body 21, but are less stiff (i.e., have a lower stiffness) than sleeve 140 and bearing member 120, where the term stiffness is used to mean to the property that relates to the rigidity of an object. For example, in some embodiments, rings 146 are constructed or formed out of steel (e.g., mild steel or carbon steel). In addition, in at least some embodiments the geometry and shape of rings 146 is chosen not only to result in the desired flexibility (previously described), but also to allow for sufficient surface area for penetration into the molded materials making up keel body 21 during molding thereof. Further, in these embodiments the geometry and shape of the rings 146 is also chosen to allow enough surface area for contact and engagement with sleeve 140 to support a weld or solder between rings 146 and sleeve 140 (which thereby prevents the disengagement of rings 146 from sleeve 140 during use of the prosthetic 10). Without being limited to this or any other theory, because rings 146 have a flexibility that is between that of the sleeve 140 and bearing member 120 and keel body 21, damage to keel body 21 caused by the transfer of forces between coupling assembly 100 and keel body 21 (particularly housing 70) during use of foot 10 is reduced. In some embodiments, after embedding member 144 is secured to radially outer surface 140c of sleeve 140 in the manner described above (e.g., welding, soldering, etc.), the sleeve 140 and embedding member 144 are both heated (e.g., in an oven) and quenched (e.g., in oil, water, etc.).

Referring still to FIGS. 3 and 4, ball 160 is spherical member that is disposed axially below sleeve 140 and bearing member 120 with respect to axis 45. Ball 160 includes a radially outer convex spherical surface 162 and a central, internally threaded bore 164 extending radially inward from outer surface 162 along axis 45. As is best shown in FIG. 3, ball 160 has a maximum outer diameter $D_{160}$.

Ball 160 is preferably constructed of a hardened aluminum alloy, such as 70-75 T6, or hard titanium alloy. Alternatively, ball 160 can be formed from stainless steel or another hard metal, but since it is desirable to minimize the weight of the components in foot 10, it is desirable to avoid using unnecessarily heavy materials such as stainless steel. In this embodiment, ball 160 is made of 70-75 T6 aluminum.

Figure 5:
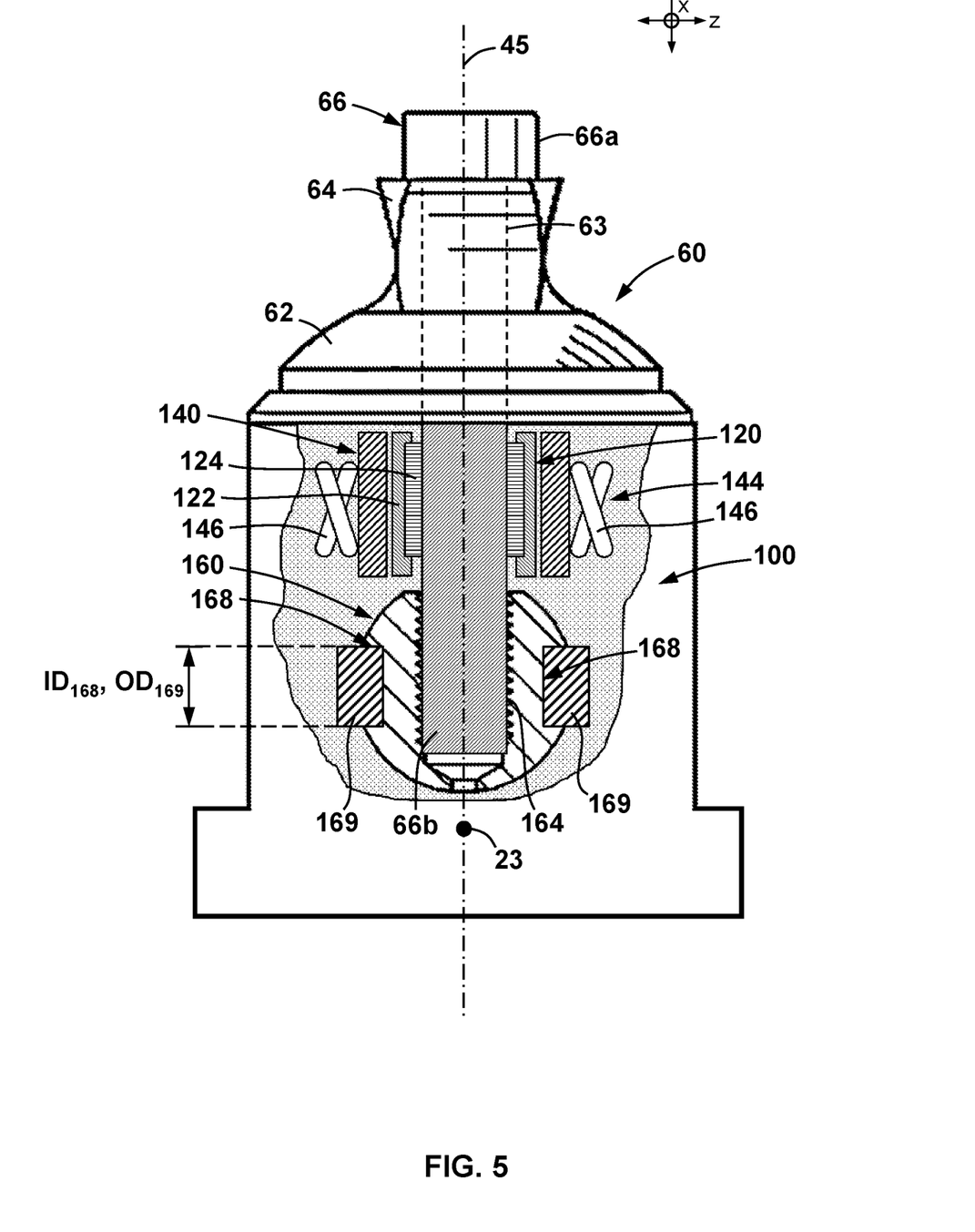
FIG. 5 is an enlarged, partial side cross-sectional view taken along section V-V of FIGS. 1 and 2.

Referring now to FIGS. 4 and 5, ball 160 includes a pair of recesses 168 that extending radially inward from outer surface 162. Each recess 168 is cylindrical in shape and is positioned on a radially opposite side of ball 160 from the other recess 168. In other words, recesses 168 are circumferentially disposed 180° from one another about radially outer convex spherical surface 162 with respect to axis 45. In this embodiment, recesses 168 are disposed on opposing sides of ball 160 in a direction that is parallel to the z-axis; however, other orientations are possible. In addition, as is best shown in FIG. 5, each recess 168 has the same inner diameter $ID_{168}$ that preferably ranges between ⅝ and 7/16 inches, inclusive.

Each recess 168 receives a corresponding cylindrical torque absorber 169 therein. Each torque absorber 169 has an outer diameter $OD_{169}$ that is preferably equal to or slightly less than the inner diameter $OD_{168}$ of the corresponding recess 168. In addition, torque absorbers 169 may be individually secured within recesses 168 (e.g., with an adhesive) prior to molding keel body 21, or they may be simply placed within recesses 168. In the latter case (i.e., where torque absorbers 169 are simply placed and not preliminarily secured within recesses 168), during molding of the keel body 21, the molded material (e.g., of body 21) flows around the torque absorbers 169 and conforms to their shape to thereby hold and secure torque absorbers 169 within recesses 168. As will be described in more detail below, during operation, torque absorbers 169 deform when spindle 64 rotates as a result of torque applied around either y-axis or the z-axis. Torque absorbers 169 preferably comprise urethane or the like, and preferably have a hardness between 50 and 90 durometer (inclusive), and more preferably 50 and 70 durometer (inclusive). Each of the torque absorbers 169 can have the same hardness (e.g., 50, 70, or 90 durometer) or can have different harnesses (e.g., in some embodiments that include 6 torque absorbers 169 on ball 160, three may have a hardness of 50 durometer and three may have a hardness of 70 durometer). In addition, the number and arrangement of the torque absorbers 169 can be greatly varied from the arrangement shown in FIGS. 3 and 5. For example, in some embodiments, ball 160 includes 4, 5, or 6, torque absorbers 169 each disposed within a corresponding recess 168 and each circumferentially disposed about axis 45 (e.g., if 6 torque absorbers 169 are included on ball 160, each is circumferentially spaced about axis 45 approximately 60° from each circumferentially adjacent torque absorber 169). In addition, in at least some embodiments, the edges of recesses 168 (e.g., at the connection between outer surface 162 and recess 168) are beveled or radiused to remove any sharp corners which may damage the torque absorbers 169 during use of prosthetic foot 10. Moreover, in addition to the features discussed above, ball 160 may be configured similar those disclosed in U.S. Pat. No. 6,511,514, the contents of which are incorporated herein by reference in their entirety for all purposes.

In this embodiment, spherical surface 162 is coated (e.g., painted) with a resilient material (e.g., silicon) prior to the installation of ball 160 within keel body 21 (e.g., through molding). Without being limited to this or any other theory, upon molding of keel body 21 around ball 160, subsequent use of the prosthetic (e.g., prosthetic 10) breaks up or pulverizes the resilient material thereby allowing relative movement between the ball 160 and keel body 21 during use. In some embodiments, lubricant (e.g., oil) may be injected at the interface between the keel body 21 and ball 160 (e.g., surface 162) which mixes with the pulverized material to further reduce friction between surface 162 and the molded material of keel body 21. The resilient material may be coated on ball 160 either before or after installation of torque absorbers 169 within recess 168. In addition, in some embodiments the resilient material coating outer surface 162 of ball may be 0.015 inches (i.e., 15 mils) thick.

Referring again to FIG. 4, the inner diameter $ID_{120}$ of bearing member 120 is preferably between ½ and ⅝ inches, inclusive. In addition, the outer diameter $OD_{120}$ of bearing member 120 and inner diameter $ID_{140}$ of housing 140 are preferably the same (or $ID_{140}$ is slightly larger than outer diameter $OD_{120}$), and further, each is preferably between ⅝ and ¾ inches, inclusive. The outer diameter $OD_{160}$ of ball 160 is preferably between 15/16 and 1 1/16 inches, inclusive.

Referring again to FIG. 4, to install coupling assembly 100 within housing 70 of ankle portion 40, outer surface 162 of ball 160 first coated in a resilient material (e.g., silicon) in the manner described above. Thereafter, the coated ball 160 (and torque absorbers 169) is inserted within a mold (not shown) for forming keel body 21, such that bore 164 is aligned with axis 45 in the manner previously described. Thereafter, bearing member 120 is inserted within support sleeve 140 and the pair (e.g., bearing member 120 and sleeve 140) are inserted within the mold (not shown) above ball such that throughbores 126, 146 of bearing member 120 and sleeve 140, respectively are axially aligned with bore 164 of ball 160 along axis 45. Connector 60 is then placed axially above bearing member 120, sleeve 140, and ball 160 such that bore 63 is aligned with throughbore 126 and bore 162. Bolt 66 is then inserted through the aligned bores 126, 164 to secure connector 60 to coupling assembly 100. Specifically, a threaded shaft 66b of bolt 66 is inserted through bore 126 and threadably engaged within bore 164 of ball 160. Torque is then applied to a head 66a of bolt 66 (e.g., with a wrench or the like) to cause rotation of bolt 66 (e.g., head 66a, and shaft 66b) about axis 45 to thereby secure connector 60 to coupling assembly 100. Thereafter, the molded material making up keel 21 is flowed into the mold (not shown) and around coupling assembly 100 to thereby embed coupling assembly 100 within the newly formed housing 70 of ankle portion 40. During the molding process, molded material flows over and around rings 146 making up embedding member 144 to firmly secure sleeve 140 to keel body 21 in the manner described above.

During use of prosthetic foot 10, stresses resulting from bending moments at the ankle portion 40 about axis 45 (e.g., about the y-axis) (i.e., dorsiflexion, planiflexion, inversion, eversion) are accommodated by coupling assembly 100 such that minimal stress is transferred to keel body 20. Specifically, bending moments in ankle portion 40 about axis 45 cause corresponding bending of shaft 66b of bolt 66 relative to bore 126 of bearing member 120. Such bending results in stress that is applied to one or more of the bearing elements 124, which then transfer to this stress to bearing race 122. The connection between elements 124 and race 122 allows at least some of these stresses to be dissipated (e.g., through deformation/movement of elements 124 relative to race 122). Stresses not dissipated by bearing members 124 and race 122 are then transferred to support sleeve 140, which then transfers any remaining stresses to housing 70 of ankle portion 40 through embedding member 144. Since the rings 146 of embedding member 144 are more flexible than support sleeve 140 (i.e., rings 146 are less stiff or have a lower stiffness value than sleeve 140), at least some of these transferred stresses are taken up by rings 146 (e.g., through deformation of rings 146) and thus are not transferred to the ankle portion 40 of keel 20. Therefore, keel body 20 sees a reduced amount of stresses that result from bending moments applied to ankle portion 40 about axis 45 (and the y-axis). Moreover, without being limited to this or any other theory, because rings 146 effectively increase the amount of surface area contact between coupling assembly 100 and keel body 20, any deformation of rings 146 (e.g., caused by bending of bolt 66 in the manner described above) is distributed along a greater area of contact with keel body 20, which therefore reduces the weakening of the bond or connection between keel body 20 and coupling assembly 100 during such use.

In addition, during these operations, bending moments about axis 45 (e.g., about the y-axis) (i.e., dorsiflexion, planiflexion, inversion, eversion) are further supported by relative rotation of keel body 21 about ball 160. Further, rotations about axis 45 (e.g., about the y-axis) are supported both by rotation of the bearing elements 124 within bearing member 120 about their respective axes 125 (e.g., see FIGS. 3 and 4) and by rotation of keel body 21 about axis 45 relative to ball 160. The rotations of body 21 relative to ball 160 during both bending and rotation about axis 45 are further facilitated by the lubricant and pulverized resilient coating disposed between keel body 21 and outer spherical surface 162 of ball 160 in the manner described above. Also, without being limited to this or any other theory, during rotation of keel body 21 about axis 45 relative to ball 160, torque absorbers 169 are deformed and therefore apply a return force that helps to urge keel body 21 back to a neutral position relative to ball 160 and the rest of coupling assembly 100 (e.g., the relative positions of keel body 21 and coupling assembly 100 shown in FIGS. 1 and 2).

In the manner described, through use of a prosthetic foot in accordance with principles disclosed herein (e.g., foot 10), stresses resulting from bending applied at the prosthetic ankle (e.g., ankle portion 40) are accommodated by an internal coupling assembly (e.g., coupling assembly 100) such that wear of the prosthetic foot is reduced. Accordingly, a prosthetic foot in accordance with principles disclosed herein (e.g., foot 10) may enjoy a longer useful life.

While exemplary embodiments have been shown and described, modifications thereof can be made by one skilled in the art without departing from the scope or teachings herein. The embodiments described herein are exemplary only and are not limiting. Many variations and modifications of the systems, apparatus, and processes described herein are possible and are within the scope of the invention. For example, while embedding member 144 has been described as including a plurality of interlocking rings 146 that are secured to radially outer surface 140c of sleeve 140, in other embodiments, embedding member 144 may comprise any suitable device(s) or member(s) that include a plurality of recesses to increase the surface area contact with the materials making up keel body 21 and is(are) more flexible and/or softer than the materials making up sleeve 140 and bearing member 120 (e.g., race 122) to help dissipate stresses at the connection point between keel body 21 and coupling assembly 100 during use of the prosthetic foot 10 as previously described. In addition, in some embodiments, one or more of the components of coupling assembly 100 (e.g., embedding member 144, sleeve 140) may be molded as one monolithic piece.

Accordingly, the scope of protection is not limited to the embodiments described herein, but is only limited by the claims that follow, the scope of which shall include all equivalents of the subject matter of the claims. Unless expressly stated otherwise, the steps in a method claim may be performed in any order. The recitation of identifiers such as (a), (b), (c) or (1), (2), (3) before steps in a method claim are not intended to and do not specify a particular order to the steps, but rather are used to simplify subsequent reference to such steps.

What is claimed is:

1. A prosthetic foot, comprising:
a keel comprising a keel body including a heel portion, a forefoot portion, and an ankle portion positioned between the heel portion and the forefoot portion, wherein the ankle portion includes a housing having a vertically oriented central axis; and
a coupling assembly embedded within the housing of the ankle portion, the coupling assembly including: a bearing member disposed about the central axis; a support sleeve concentrically disposed about the bearing member; and an embedding member disposed about the support sleeve, wherein the embedding member includes a plurality of interlocking rings.

2. The prosthetic foot of claim 1, wherein the coupling assembly further comprises a ball including an internally threaded bore aligned with the central axis; wherein the ball is disposed axially adjacent the bearing member and the support sleeve along the central axis.

3. The prosthetic foot of claim 2, further comprising a connector coupled to the ankle portion, the connector including:
a semi-spherical dome;
a connector spindle; and
a throughbore.

4. The prosthetic foot of claim 3, further comprising a bolt including an externally threaded shaft that extends through the throughbore of the connector and the bearing member, wherein the externally threaded shaft is threadably received within the internally threaded bore of the ball.

5. The prosthetic foot of claim 4, wherein the bearing member comprises a needle bearing.

6. The prosthetic foot of claim 5, wherein one or more of the interlocking rings of the embedding member is welded to a radially outer surface of the support sleeve.

7. The prosthetic foot of claim 1, wherein a material of the keel body has a first stiffness, the interlocking rings of the embedding member have a second stiffness, and the support sleeve has a third stiffness, and
wherein the second stiffness is greater than the first stiffness and is less than the third stiffness.

8. The prosthetic foot of claim 1, comprising a cosmesis disposed about the keel.

9. The prosthetic foot of claim 1, comprising a pair of bumpers disposed on opposite sides of the housing of the ankle portion.

10. The prosthetic foot of claim 9, wherein the bumpers have a lower durometer hardness than the keel.

11. The prosthetic foot of claim 9, wherein each of the pair of bumpers is disposed within a corresponding cavity formed in the ankle portion.

12. The prosthetic foot of claim 9, wherein the keel includes a longitudinal axis, a heel end, and a toe end,
wherein the heel end is spaced from the toe end along the longitudinal axis,
wherein a first of the pair of bumpers is disposed between the coupling assembly and the heel end along the longitudinal axis of the keel, and wherein a second of the pair of bumpers is disposed between the coupling assembly and the toe end along the longitudinal axis of the keel.

13. The prosthetic foot of claim 12, wherein each of the bumpers is cylindrical in shape and extends in a direction that is perpendicular to a direction of the longitudinal axis of the keel.

14. A method of making a prosthetic foot, the method comprising:
 installing a coupling assembly within a mold, the coupling assembly including:
  a bearing member disposed about a vertically oriented central axis;
  a support sleeve concentrically disposed about the bearing member; and
  an embedding member disposed about the support sleeve, wherein the embedding member includes a plurality of interlocking rings secured to an outer surface of the support sleeve;
 filling the mold with a material such that the material flows around and through the interlocking rings of the embedding member; and
 forming a keel of the prosthetic foot out of the material, wherein the keel comprises a keel body including a heel portion, a forefoot portion, and an ankle portion positioned between the heel portion and the forefoot portion, wherein the ankle portion includes a housing, and wherein the coupling assembly is embedded within the housing of the ankle portion.

15. The method of claim 14, wherein the coupling assembly further comprises:
 a ball including an internally threaded bore aligned with the central axis; and
 a bolt including an externally threaded shaft; and
 wherein installing the coupling assembly within the mold further comprises:
  inserting the ball within the mold such that it is axially adjacent the bearing member and the support sleeve along the central axis;
  inserting the threaded shaft of the bolt through the bearing member; and
  threadably receiving the threaded shaft of the bolt within the threaded bore of the ball.

16. The method of claim 15, further comprising inserting the threaded shaft of the bolt through a throughbore of a connector, wherein the connector further comprises:
 a semi-spherical dome; and
 a connector spindle.

17. The method of claim 16, wherein filling the mold with a material further comprises securing the material to the connector.

18. The method of claim 14, further comprising coating the ball with a resilient material prior to inserting the ball within the mold.

19. The method of claim 18, wherein coating the ball with the resilient material comprises coating the ball with silicon.

* * * * *